(12) United States Patent
Varghese et al.

(10) Patent No.: US 9,126,965 B1
(45) Date of Patent: Sep. 8, 2015

(54) PROCESS FOR PREPARING MORPHINE COMPOUNDS

(71) Applicants: Vimal Varghese, St. Catharines (CA); Tomas Hudlicky, St. Catharines (CA)

(72) Inventors: Vimal Varghese, St. Catharines (CA); Tomas Hudlicky, St. Catharines (CA)

(73) Assignee: Brock University, St. Catharines, Ontario (CA)

( * ) Notice: Subject to any disclaimer, the term of this patent is extended or adjusted under 35 U.S.C. 154(b) by 0 days.

(21) Appl. No.: 14/628,333

(22) Filed: Feb. 23, 2015

Related U.S. Application Data

(60) Provisional application No. 61/943,556, filed on Feb. 24, 2014.

(51) Int. Cl.
*C07D 307/77* (2006.01)
*C07F 7/18* (2006.01)

(52) U.S. Cl.
CPC ............ *C07D 307/77* (2013.01); *C07F 7/1892* (2013.01)

(58) Field of Classification Search
USPC ........................................................ 549/457
See application file for complete search history.

(56) References Cited

PUBLICATIONS

Hudlicky, Tomas et al., "A Model Study Directed Towards a Practical Enantioselective Total Synthesis of (−)-Morphine", Synthesis, pp. 174-178, Jan./Feb. 1992.

Butora, Gabor et al., "Advanced Intramolecular Diels-Alder Study Toward the Synthesis of (−)-Morphine: Structure Correction of a Previously Reported Diels-Alder Product", Synthesis, pp. 275-278, Mar. 1998.

Tius, Marcus A., "A Novel Approach to the Synthesis of Morphine Alkaloids: The Synthesis of (d,l)-Thebainone-A", J. Am. Chem. Soc., 1992, 114, pp. 5959-5966.

Carlini, Rina, et al., "Diels-Alder adducts of ortho-benzoquinones: rearrangements and further transformations", Can. J. Chem. 75: pp. 805-816, 1997.

Carlini, Rina, et al., "Three step syntheses of naphthofurans and phenanthrofurans related to (−)-mrophine from ortho-benzoquinone monoketals by Diels-Alder and Cope reactions", Chem. Commun., 1998, pp. 65-66.

Gao, Jihong, et al., "From Chiral ortho-Benzoquinone Monoketals to Nonracemic Indolinocodeines through Diels-Alder and Cope Reactions", J. Org. Chem. 2013, 78, pp. 48-58.

Lang, Yunhui, et al., "Pentacyclic Furanosteriods: The Synthesis of Potential Kinase Inhibitors Related to Viridin and Wortmannolone", J. Org. Chem., 2009, 74, pp. 5429-5439.

Souza, Fabio E.S., et al., "Progress towards viridin: synthesis of the pentacyclic furanosteroid ring system via o-benzoquinoid cycloadditions", Chem. Commun., 1999, pp. 1947-1948.

Sutherland, Hamish S., et al, "Isobenzofurans and ortho-benzoquinone monoketals in syntheses of xestoquinone and its 9- and 10-methoxy derivatives", Tetrahedron 57 (2001), pp. 309-317.

Carlini, Rina et al., "Intramolecular Diels-Alder and Cope Reactions of o-Quinonoid Monoketals and Their Adducts: Efficient Syntheses of (±)-Xestoquinone and Heterocycles Related to Viridin", J. Org. Chem., 1997, 62, pp. 2330-2331.

*Primary Examiner* — Kristin Vajda
(74) *Attorney, Agent, or Firm* — Bereskin & Parr LLP/S.E.N.C.R.L., s.r.l.; Patricia Folkins

(57) ABSTRACT

The present application relates to processes for the preparation of morphine compounds utilizing a novel intramolecular [4+2] cycloaddition reaction.

12 Claims, No Drawings

PROCESS FOR PREPARING MORPHINE COMPOUNDS

CROSS-REFERENCE TO RELATED APPLICATIONS

The present application claims the benefit of priority from U.S. provisional application No. 61/943,556 filed on Feb. 24, 2014, the contents of which are incorporated herein by reference in their entirety.

FIELD

The present application relates to processes for the preparation of morphine compounds. In particular, the present application relates to a novel process for forming the morphine skeleton using a [4+2] intramolecular cycloaddition reaction.

BACKGROUND

A truly practical synthesis of morphine and congeners has not yet appeared in spite of focused effort and many creative approaches having been published.[1]

SUMMARY

In one embodiment, the present application includes a process for the preparation of a compound of Formula I comprising treating a compound of Formula II under [4+2] intramolecular cycloaddition conditions:

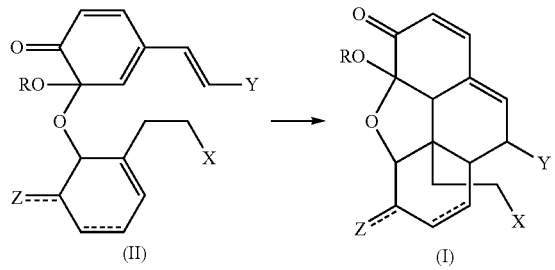

wherein:
---- represents a single or double bond;
Z is O when Z ---- represents a double bond and Z is OPG$^1$ when Z ---- represents a single bond;
OR represents a leaving group;
at least one of Y and X is NMePG$^2$ and the other is LG, or Y is H and X is NMePG$^2$;
PG$^1$ and PG$^2$ are, independently, protecting groups; and
LG is a leaving group, and
one or more available hydrogens in the compounds of Formulae I and II is/are optionally replaced with F and/or one or more of available atoms in the compounds of Formulae I and II is/are optionally replaced with an isotopic label.

Processes for preparing compounds of Formula II, and precursors thereof, are described and included in the present application, as well as the conversion of the compounds of Formula I into various morphine compounds.

It has been demonstrated that the process of the present application is enantiodivergent. For example, an enantiomer of hydromorphone (ent-hydromorphone) has been made and the other enantiomer is readily available using the same process.

The present application also includes any of the novel compounds disclosed herein. In particular, the present application includes compounds 5, 6, 17, 18, 19a, 19b, 20, 21, 23, 24, 25 and 26 as shown in Schemes 1 and 4 hereinbelow.

Other features and advantages of the present application will become apparent from the following detailed description. It should be understood, however, that the detailed description and the specific examples while indicating embodiments of the application are given by way of illustration only and the scope of the claims should not be limited by the embodiments set forth in the examples, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions for the reaction to proceed to a sufficient extent to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process/method steps disclosed herein means that the reactions or process/method steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a compound" should be understood to present certain aspects with one compound or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

In embodiments of the present application, the compounds in the processes/methods described herein have at least one asymmetric center. Where compounds possess more than one asymmetric center, they may exist as diastereomers. It is to be understood that all such isomers and mixtures thereof in any proportion are encompassed within the scope of the processes/methods of the present application. It is to be further understood that while the stereochemistry of the compounds in the processes/methods may be as shown in any given compound listed herein, such compounds may also contain certain amounts (e.g. less than 20%, suitably less than 10%, more suitably less than 5%) of compounds having alternate stereochemistry.

The term "protecting" as used herein refers to using a chemical moiety, i.e. a "protecting group" of "PG" which protects or masks a reactive portion of a molecule to prevent side reactions in that reactive portion of the molecule, while manipulating or reacting a different portion of the molecule. After the manipulation or reaction is complete, the protecting group is removed under conditions that do not degrade or decompose the remaining portions of the molecule; i.e. the protected reactive portion of the molecule is "deprotected". The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include, but are not limited to t-Boc, $C_{1-6}$acyl, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

The term "leaving group" or "LG" as used herein refers to a group that is readily displaceable by a nucleophile, for example, under nucleophilic substitution reaction conditions. Examples of suitable leaving groups include, but are not limited to, halo, OMs, OTs, ONs, OTf, $OC_{1-6}$acyl, and the like, including isotopically labeled versions thereof.

The term "acyl" as used herein, whether it is used alone or as part of another group, means straight or branched chain, saturated acyl groups. The number of carbon atoms that are possible in the referenced acyl group are indicated by the numerical prefix "$C_{n1-n2}$". For example, the term $C_{1-6}$acyl means an acyl group having 1, 2, 3, 4, 5 or 6 carbon atoms.

The term "halo" as used herein refers to a halogen atom and includes F, Cl, Br and I.

The term "oxidizing agent" as used herein means any compound or combination of compounds that oxidizes a desired functional group(s) but does not otherwise react with or degrade the substrate comprising the functional group(s). An oxidizing agent results in the overall loss of electrons, or in the case of organic chemistry, hydrogen atoms from the functional group.

The term "reducing agent" as used herein means any compound or combination of compounds that reduces a desired functional group(s) but does not otherwise react with or degrade the substrate comprising the functional group(s). A reducing agent results in the overall gain of electrons, or in the case of organic chemistry, hydrogen atoms to the functional group. It is an embodiment of the application that the reducing agent is a metal hydride reducing agent.

The term "inert solvent" as used herein means a solvent that does not interfere with or otherwise inhibit a reaction. Accordingly, the identity of the inert solvent will vary depending on the reaction being performed. The selection of inert solvent is within the skill of a person in the art. Examples of inert solvents include, but are not limited to, benzene, toluene, tetrahydrofuran, ethyl ether, ethyl acetate, dimethyl formamide (DMF), acetonitrile, $C_{1-6}$alkylOH (e.g. methanol, ethanol, n-propanol, 2-propanol, n-butanol, butan-2-ol and 2-methyl-1-propanol), diethylcarbonate, hexane and dimethylsulfoxide (DMSO) including isotopically labeled versions thereof. Further examples can include aqueous solutions, such as water and dilute acids and bases, and ionic liquids, provided that such solvents do not interfere with the reaction.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms.

The term "solvent" includes both a single solvent and a mixture comprising two or more solvents.

The term "available", as in "available hydrogen atoms" or "available atoms" refers to atoms that would be known to a person skilled in the art to be capable of replacement by either a fluorine atom (in the case of hydrogen atoms) or isotopic labels (in the case of all atoms) using methods known in the art.

The term "counteranion" as used herein refers to a negatively charged species consisting of a single element, or a negatively charged species consisting of a group of elements connected by ionic and/or covalent bonds.

t-Boc as used herein refers to the group t-butyloxycarbonyl.

Ac as used herein refers to the group acetyl.

Ts (tosyl) as used herein refers to the group p-toluenesulfonyl.

Ms as used herein refers to the group methanesulfonyl.

TBDMS as used herein refers to the group t-butyldimethylsilyl.

TBDPS as used herein refers to the group t-butyldiphenylsilyl.

TMS as used herein refers to the group trimethylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

The term "morphine compound" as used herein refers to a compound containing the 5 ring morphine skeleton as follows:

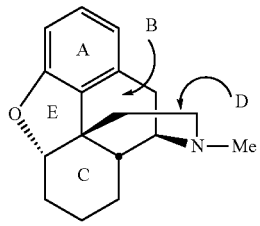

with optional substituents on one or more of the ring atoms and optional double bonds in ring C. In an embodiment, the morphine compound is ent-hydromorphone or hydromorphone.

The term "oripavine" as used herein refers to a compound of the following formula:

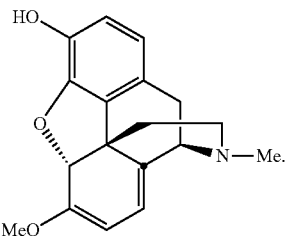

The term "hydromorphone" as used herein refers to a compound of the following formula:

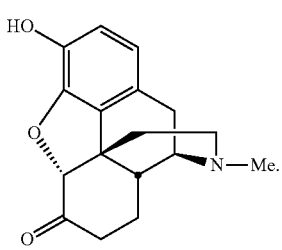

The term "ent-hydromorphone" as used herein refers to a compound of the following formula:

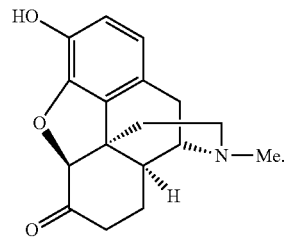

The term "thebaine" as used herein refers to a compound of the following formula:

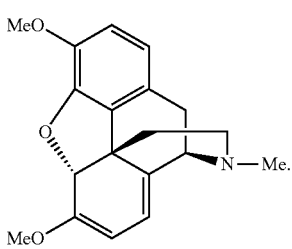

The term "morphine" as used herein refers to a compound of the following formula:

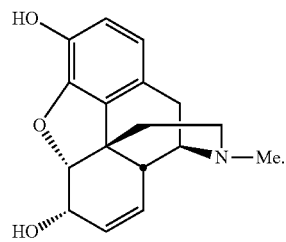

II. Processes

In the present application a strategy to construct the morphine skeleton by an intramolecular [4+2] cycloaddition reaction is reported. A schematic of a representative example of the overall strategy as it applies to the preparation of hydromorphine and ent-hydromorphine is shown in Scheme 1:

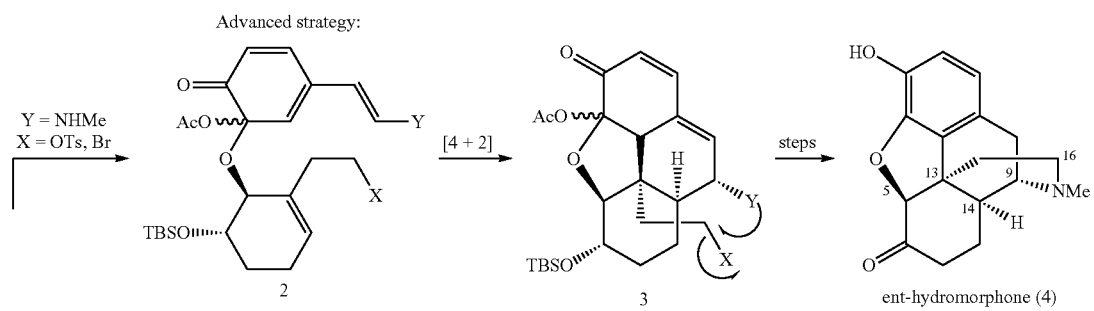

Scheme 1

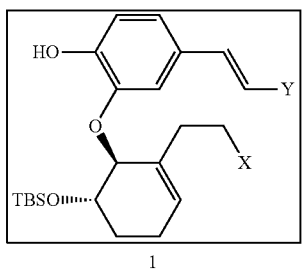

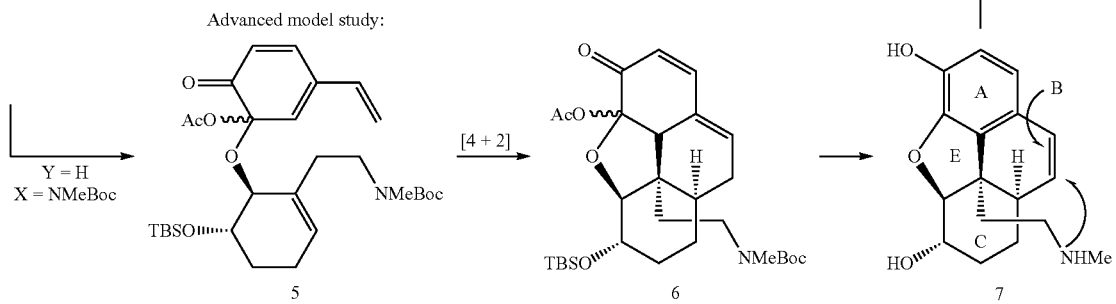

Therefore, in one embodiment, the present application includes a process for the preparation of a compound of Formula I comprising treating a compound of Formula II under [4+2] intramolecular cycloaddition conditions:

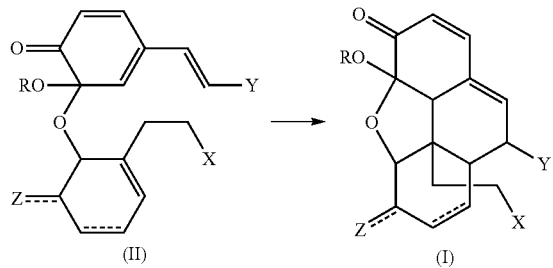

wherein:
---- represents a single or double bond;
Z is O when Z ---- represents a double bond and Z is OPG$^1$ when Z ---- represents a single bond;
OR represents a leaving group;
at least one of Y and X is NMePG$^2$ and the other is LG, or Y is H and X is NMePG$^2$;
PG$^1$ and PG$^2$ are, independently, protecting groups; and
LG is a leaving group, and
one or more available hydrogens in the compounds of Formulae I and II is/are optionally replaced with F and/or one or more of available atoms in the compounds of Formulae I and II is/are optionally replaced with an isotopic label.

In an embodiment, the compound of Formula II is derived from the corresponding phenol by oxidative dearomatization using, for example, lead tetraacetate (Pb(OAc)$_4$), diacetoxy-iodobenzene (DAIB), bis trifluoroacetoxyiodo benzene (PIFA) or Dess-Martin periodinane. In another embodiment, the oxidative dearomatization comprises electrochemical anodic oxidation. The selection of suitable conditions for electrochemical anodic oxidation can be made by a person skilled in the art.

Accordingly, in a further embodiment, the present application includes a process of preparing a compound of Formula I comprising converting a compound of Formula III into a compound of Formula II by oxidative dearomatization followed by treating the compound of Formula II under [4+2] intramolecular cycloaddition conditions to provide the compound of Formula I:

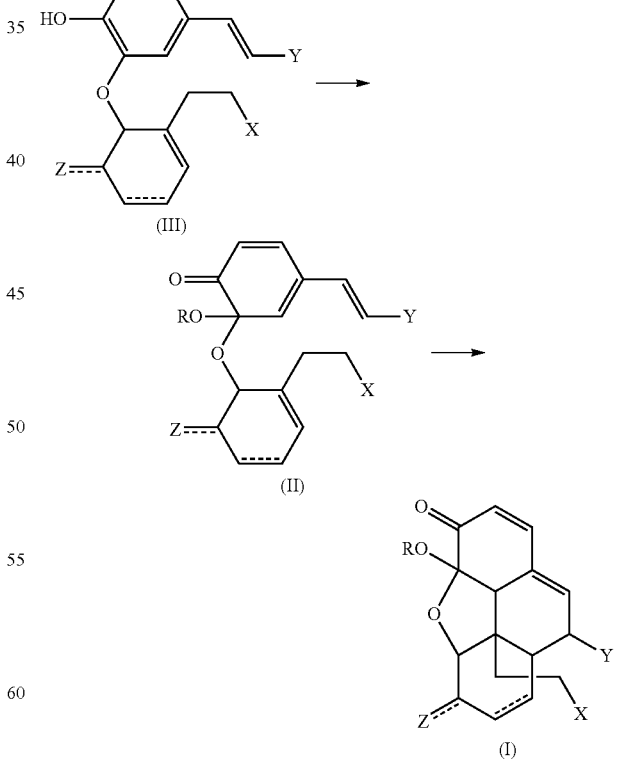

wherein:
---- represents a single or double bond;
Z is O when Z ---- represents a double bond and Z is OPG$^1$ when Z ---- represents a single bond;

OR represents a leaving group;
at least one of Y and X is NMePG² and the other is LG,
or Y is H and X is NMePG²;
PG¹ and PG² are, independently, protecting groups; and
LG is a leaving group, and
one or more available hydrogens in the compounds of Formulae I-III is/are optionally replaced with F and/or one or more of available atoms in the compounds of Formulae I-III is/are optionally replaced with an isotopic label.

In an embodiment, the compound of Formula III is available by reacting a compound of the Formula IV with a compound of the Formula V under Mitsunobu reaction conditions to provide a compound of the Formula VI followed by Wittig homologation of the CHO group and removal of PG³:

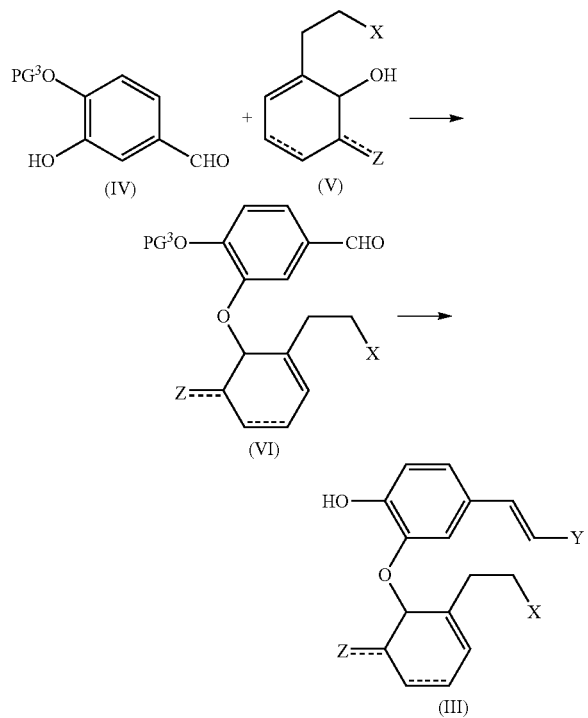

wherein:
---- represents a single or double bond;
Z is O when Z ---- represents a double bond and Z is OPG¹ when Z ---- represents a single bond;
at least one of Y and X is NMePG² and the other is LG,
or Y is H and X is NMePG²;
PG¹, PG² and PG³ are, independently, protecting groups; and
LG is a leaving group, and
one or more available hydrogens in the compounds of Formulae III-VI is/are optionally replaced with F and/or one or more of available atoms in the compounds of Formulae III-VI is/are optionally replaced with an isotopic label.

In an embodiment, the Wittig homologation of CHO in the compound of Formula VI is performed by reacting a compound of the Formula VI with a Wittig reagent, for example, a compound of the Formula VII:

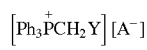  (VII)

wherein A− is a suitable counteranion and Y is as defined above, under Wittig reaction conditions.

In another embodiment, the compound of the Formula III wherein Y is H is prepared by Wittig homologation of the CHO group in a compound of Formula X to provide a compound of Formula XI, followed by selective removal of PG⁵ to provide a compound of Formula XII, then reacting the compound of Formula XII with a compound of Formula V under Mitsunobu reaction conditions and removal of PG⁴:

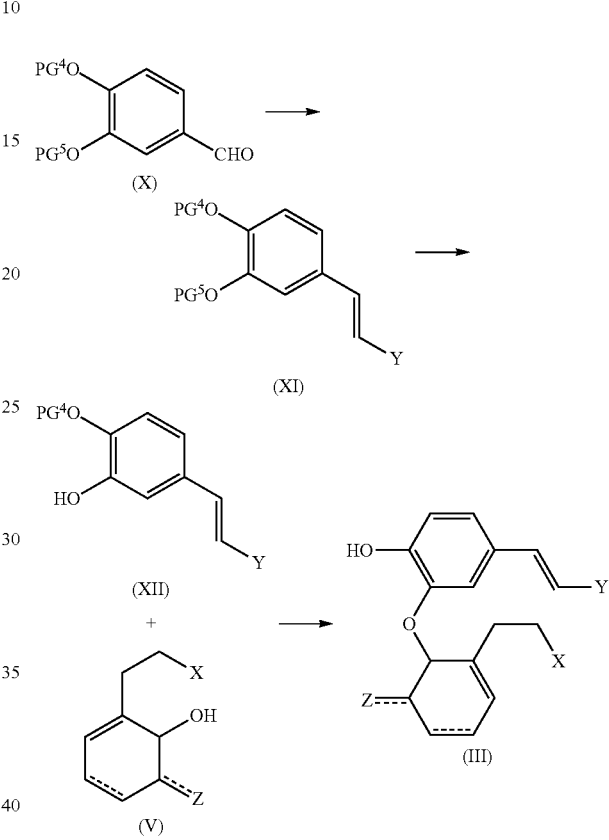

wherein:
---- represents a single or double bond;
Z is O when Z ---- represents a double bond and Z is OPG¹ when Z ---- represents a single bond;
at least one of Y and X is NMePG² and the other is LG,
or Y is H and X is NMePG²; and
PG², PG⁴ and PG⁵ are, independently, protecting groups, wherein PG⁴ and PG⁵ are protecting groups that are removable under different conditions.

In an embodiment, the Wittig homologation of CHO in the compound of Formula X is performed by reacting a compound of the Formula X with a Wittig reagent, for example, a compound of the Formula VII:

  (VII)

wherein A− is a suitable counteranion and Y is as defined above, under Wittig reaction conditions.

Compounds of the Formula V, when X is NMePG², Z is OPG¹ and Z ---- and C ---- C are both single bonds, are available, for example, using methods known in the art, for example from (2-bromoethyl)benzene as described in the literature[4,5] and as shown in Scheme 3 below. Alternatively, compounds of the Formula V, when Z is O, Z ---- is a double bond and C—C is a single bond, are prepared, for example, by the Birch reduction of a compound of the Formula VIII to provide a compound of the Formula IX, wherein X is as defined above. A Davis hydroxylation, which can be performed asymmetrically to provide either enantiomer, is then used to convert the compound of the Formula IX into the compound of the Formula V. The present application therefore also includes a process for preparing a compound of the Formula V, wherein X is NMePG$^2$ or LG, Z is O, Z ---- is a double bond and C ---- C is a single bond comprising treating a compound of the Formula VIII under Birch reduction conditions to provide a compound of the Formula IX and treating the compound of the Formula IX under Davis hydroxylation conditions to provide the compound of the Formula V, wherein X is NMePG$^2$ or LG, Z is O, Z ---- is a double bond and C ---- C is a single bond:

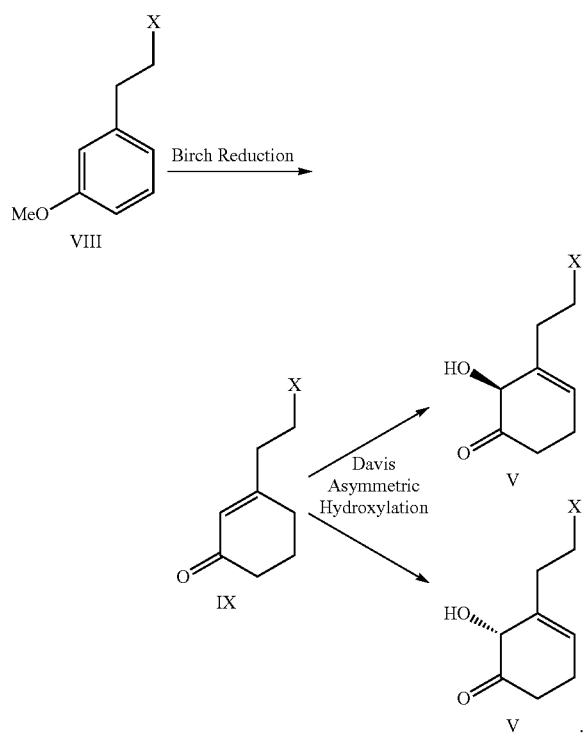

Compounds of the Formula IV, are known and are prepared, for example, from 3,4-dihydroxylbenzaldyde as described in the literature[2] and as shown in Scheme 2 below.

Compounds of the Formula VII, VIII and X are either known in the art or are prepared using methods known in the art.

In an embodiment, Z ---- and C ---- C both represent single bonds. Therefore, in an embodiment, Z is OPG$^1$.

In an embodiment, Y is H and X is NMePG$^2$.

In another embodiment, X is LG and Y is NMePG$^2$.

In an embodiment, OR is OAc.

In an embodiment, the stereochemistry of the compounds of Formula II-XII is selected so that the compound of Formula I has the same stereochemistry as that found in hydromorphone. In an embodiment, the stereochemistry of the compounds of Formula II-XII is selected so that the compound of Formula I has the same stereochemistry as that found in ent-hydromorphone.

In an embodiment, the intramolecular cycloaddition conditions comprise heating a substrate, i.e. a compound comprising a diene and a dienophile such as a compound of Formula II, in an inert organic solvent, optionally in the presence of a catalyst.

In a further embodiment, oxidative dearomatization conditions comprise treating an appropriate aromatic substrate with a suitable oxidizing agent, such as Pb(OAc)$_4$, diacetoxyiodobenzene (DAIB), bis trifluoroacetoxyiodo benzene (PIFA) or Dess-Martin periodinane, in an inert organic solvent, optionally with heating. In a further embodiment, the oxidative dearomatization to provide the compounds of Formula II and intramolecular cycloaddition are performed in a single step, wherein the compound of Formula II is formed in situ and converted, under the oxidative dearomatization conditions to a compound of the Formula I. In an embodiment, the oxidizing agent is Pb(OAc)$_4$.

In an embodiment, the Mitsunobu reaction conditions comprise treating the substrates in the presence of a trialkylphosphine, or a triarylphosphone, and an azodicarboxylate, such as tetramethylazodicarboxamide (TMAD), diethylazodicarboxylate (DEAD) or diisopropylazodicarboxylate (DIAD) in an inert organic solvent. The reaction conditions optionally comprise heating or cooling depending on the substrates as would be known to a person skilled in the art.

In an embodiment, Wittig homologation refers to the conversion of an aldehyde to the next higher homolog (i.e. addition of one methylene unit) using Wittig reaction conditions.

In an embodiment, Wittig reaction conditions comprise reaction of an aldehyde-containing substrate with a Wittig reagent, for example a compound of the Formula VII as defined above at low temperature (for example, −50° C. to −100° C.) in an inert organic solvent, followed by warming to, for example room temperature or above, In an embodiment, Birch reduction conditions comprise reaction of an aromatic substrate, such as a compound of Formula VIII, with anhydrous ammonia, t-BuOH and metals such as Na, Li etc. at low temperature (for example, −50° C. to −100° C.) in an inert organic solvent, followed by warming to, for example room temperature or above, and treating with a suitable acid to provide, for example, the desired enone IX.

In an embodiment, Davis hydroxylation conditions comprise reaction of an enone, for example a compound of Formula IX, with metal bases at low temperature (for example, −50° C. to −100° C.) in an inert organic solvent, followed by reacting with Davis oxaziridine (or equivalent reagent) at low temperature (for example, −50° C. to −100° C.), quenching the reaction with a suitable acid to provide, for example, the desired alcohol V.

Standard methods and reactions are used to convert the compound of Formula I into morphine compounds. For example, when one of X and Y is NMePG$^2$ and the other is LG, removal of PG$^2$ followed by nucleophilic displacement of the LG leads to the formation of the ring D of the morphine skeleton. In another example, when Y is H and X is NMePG$^2$, formation of ring D is carried out using reductive cyclization, such as nitrogen centered radical cyclization. Oxidation and/or reduction of the various functional groups, such as the C6 OH group, as well as removal of protecting groups are performed to provide the desired morphine compound.

The following non-limiting examples are illustrative of the present application:

EXAMPLES

The reactions and numbering referred to in Examples 1 and 2 are depicted in Scheme 2:

Scheme 2

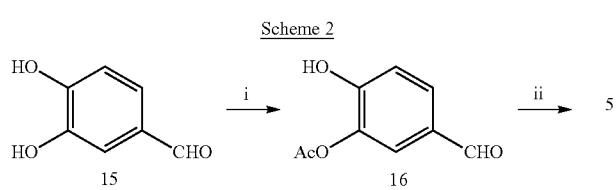

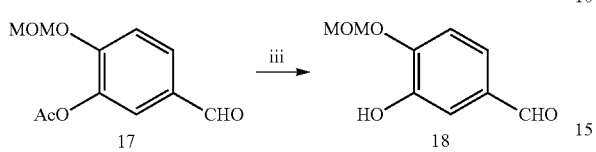

Scheme 2. (i) Ac$_2$O, NaOH, THF, 0° C., 82-85%; (ii) MOMCl, K$_2$CO$_3$, DMF, 0° C. to rt, 76-80%; (iii) K$_2$CO$_3$, MeOH, rt, 88-90%.

Example 1

4-Formyl-2-hydroxyphenyl acetate (16)

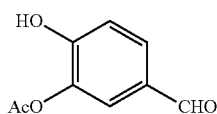

Aldehyde 15[2] (3.9 g, 28 mmol) was dissolved in THF and the solution was cooled to 0° C. Then a 2 N solution of NaOH in water (70 mmol) was added dropwise followed by the addition of acetic anhydride (3.2 mL, 34 mmol). The reaction mixture was stirred for 20 minutes, diluted with EtOAc, made acidic with 2.5 mL of con. HCl and 20 mL of phosphate buffer (pH=2.5). Then it was filtered through a pad of Celite™ and the organic phase was separated. The aqueous phase was washed 3 times with EtOAc, organic washes were combined, washed with brine, dried over Na$_2$SO$_4$ and solvent was evaporated under reduced pressure to obtain the crude product, which was purified by suction filtration chromatography on silica gel with [CH$_2$Cl$_2$/MeOH (98:2)→CH$_2$Cl$_2$/MeOH (95:5)] as eluent to provide 16 as a light yellow solid (4.2 g, 23.3 mmol, 84%). It was recrystallized from ether to provide colourless crystals.

m.p. 88-91° C. (ether), [lit.[3] 87-89° C. (ether-light petrol)]; R$_f$=0.33 [CH$_2$Cl$_2$/MeOH (98:2)]; IR (CHCl$_3$, cm$^{-1}$) ν 3564, 3374, 3028, 2838, 2737, 1773, 1696, 1607, 1509, 1441, 1371, 1296, 1277, 1172; $^1$H NMR (300 MHz, CDCl$_3$) δ 9.78 (s, 1H), 7.69 (dd, J=8.4 Hz, 1.8, 1H), 7.58 (d, J=2.1 Hz, 1H), 7.07 (d, J=8.4 Hz, 1H), 4.95 (bs, 1H), 2.33 (s, 3H); $^{13}$C NMR (150 MHz, CDCl$_3$) δ 191.8, 169.3, 155.4, 139.1, 129.6, 129.1, 124.0, 116.7, 19.2; MS (EI) m/z (%) 180 (11), 138 (65), 137 (55), 43 (100); HRMS (EI) calcd for C$_9$H$_8$O$_4$: 180.0423. Found 180.0427; Anal. Calcd for C$_9$H$_8$O$_4$: C, 60.00; H, 4.48. Found C, 60.24; H, 4.59.

Example 2

3-Hydroxy-4-(methoxymethoxy)benzaldehyde (18)

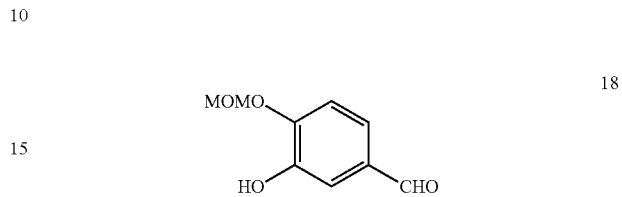

To a suspension of K$_2$CO$_3$ (2.3 g, 16.8 mmol) in DMF (30 mL) at 0° C. was added MOMCl (0.84 mL, 2 mmol) dropwise. Then a solution of 16 (1 g, 5.6 mmol) in DMF (30 mL) was added dropwise through an addition funnel. The reaction mixture was allowed to stir for another 30 minutes and was diluted with H$_2$O (100 mL). It was then extracted three times with Et$_2$O (75 mL), organic washes were combined, washed with brine solution, dried over Na$_2$SO$_4$, and the solvent was evaporated under reduced pressure to provide the crude acetate 17 which was taken to next step without further purification.

A saturated solution of K$_2$CO$_3$ in MeOH (15 mL) was added to a solution of acetate 17 in MeOH (10 mL) at room temperature. The reaction mixture was stirred at room temperature for 40 minutes, then the pH of the reaction mixture was adjusted to 7 using 1 N HCl and NH$_4$Cl (saturated) solution. The aqueous layer was extracted with CH$_2$Cl$_2$ (3×100 mL), washed with brine, dried over Na$_2$SO$_4$, and the volatiles were removed in vacuo to provide crude product, which was filtered through a plug of silica using EtOAc to yield 18 (0.72 g, 3.95 mmol, 71% over two steps) as a colourless liquid.

R$_f$=0.15 [hexane/EtOAc (80:20)]; IR (CHCl$_3$, cm$^{-1}$) ν 3615, 3028, 3007, 2964, 2740, 1705, 1578, 1464; $^1$H NMR (CDCl$_3$, 300 MHz) δ 9.79 (s, 1H), 7.42 (d, J=1.8 Hz, 1H), 7.35 (dd, J=8.4, 1.8 Hz, 1H), 7.17 (d, J=8.4 Hz, 1H), 6.54 (s, 1H), 5.26 (s, 2H), 3.47 (s, 3H); $^{13}$C NMR (CDCl$_3$, 75 MHz) δ 191.4, 149.8, 146.7, 131.4, 124.3, 114.9, 114.3, 95.2, 56.6; MS (EI) m/z (%) 182 (13), 45 (100); HRMS-EI calcd for C$_9$H$_{10}$O$_4$: 182.0579 found 182.0576.

The reactions and numbering referred to in Examples 3-4 are depicted in Scheme 3:

Scheme 3

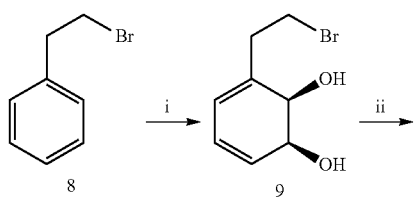

-continued

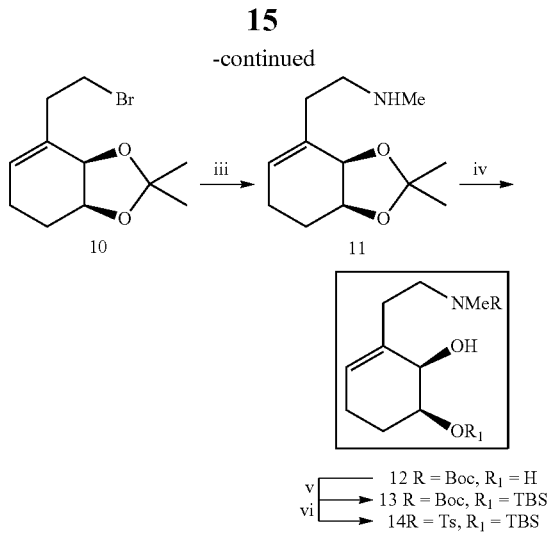

Scheme 3. (i) *E. coli* JM 109 (pDTG601A), 10-15 g/L; (ii) (a) potassium azodicarboxylate, AcOH, MeOH, 0° C., 83%; (b) 2,2-dimethoxypropane, acetone, pTsOH, 80%; (iii) MeNH$_2$, K$_2$CO$_3$, THF, sealed tube, 93%; (iv) (a) 3 mol/L HCl, EtOH; (b) Boc$_2$O, NaHCO$_3$, EtOH, 74% (2 steps); (v) TBSCl, imidazole, CH$_2$Cl$_2$, −78° C. to rt, 92%; (vi) (a) TFA, CH$_2$Cl$_2$, 0° C.; (b) TsCl, Et$_3$N, CH$_2$Cl$_2$, rt, 86% over two steps.

Example 4a

N-(2-((5S,6R)-5-((tert-Butyldimethylsilyl)oxy)-6-hydroxycyclohex-1-en-1-yl)ethyl)-N,4-dimethylbenzenesulfonamide (13)

The synthesis of the homochiral subunit 13 was accomplished as shown in Scheme 3 and as previously described.[4,5] Dihydroxylation of 8 by whole-cell fermentation with *E. coli* JM 109 (pDTG601A)[6] yielded 9, which was immediately subjected to a selective reduction with potassium azodicarboxylate, followed by protection of the diol to give 10. Displacement of bromine in 10 with methylamine produced 11 (the tosylation of this compound could be used in the future to provide 14 and hence 19b, Scheme 4, in a more direct way). Hydrolysis of the acetonide with HCl was followed by protection of the secondary amine as a Boc carbamate to provide 12 in a one-pot operation; regioselective silylation of the distal hydroxyl then provided alcohol 13.

Example 4b

N-(2-((5S,6R)-5-((tert-Butyldimethylsilyl)oxy)-6-hydroxycyclohex-1-en-1-yl)ethyl)-N,4-dimethylbenzenesulfonamide (14)

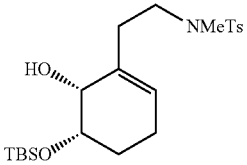

To a solution of 13 (1 g, 2.59 mmol) in CH$_2$Cl$_2$ at 0° C. was added TFA (4 mL, 32 mmol) and was stirred for 20 minutes. Then the reaction mixture was diluted with CH$_2$Cl$_2$ (60 mL), then saturated NaHCO$_3$ solution was added and pH was adjusted to ~9. The organic layer was separated and the aqueous layer was washed with CH$_2$Cl$_2$ (3×30 mL), the organic washes were combined and were washed with brine solution, dried over Na$_2$SO$_4$ and solvent was evaporated under reduced pressure to provide crude product (540 mg). Then the aqueous phase was saturated with NaCl and was washed with CHCl$_3$: EtOH (3:1) (3×30 mL), dried over Na$_2$SO$_4$ and solvent was evaporated under reduced pressure to provide another 200 mg of crude product. The crude material was taken to the next step without further purification.

To a solution of crude product (740 mg, 2.6 mmol) in CH$_2$Cl$_2$ at 0° C. was added Et$_3$N (0.47 mL, 3.37 mmol) followed by TsCl (593 mg, 3.1 mmol). The reaction mixture was slowly warmed to room temperature and was stirred for 3 hours. Then the solvent was evaporated under reduced pressure and column chromatography on silica gel using [hexane/EtOAc (90:10)→hexane/EtOAc (70:30)] to provide 14 (979 mg, 2.2 mmol, 86%) as a clear liquid.

R$_f$=0.12 [hexane/EtOAc (70:30)]; [α]$^{20}_D$=−30.0 (c=1.15, CHCl$_3$); IR (CHCl$_3$, cm$^{-1}$) ν 3550, 3028, 3008, 2954, 2930, 2885, 2859, 1690, 1598, 1462, 1373, 1339, 1160, 1088; $^1$H NMR (CDCl$_3$, 300 MHz) δ 7.64 (d, J=8.1 Hz, 2H), 7.27 (d, J=8.1 Hz, 2H), 5.58 (bs, 1H), 3.92 (d, J=3.6 Hz, 1H), 3.83-3.78 (m, 1H), 3.35-3.26 (m, 1H), 3.00-2.93 (m, 1H), 2.70 (s, 3H), 2.39 (s, 4H), 2.30-2.23 (m, 1H), 2.21-1.88 (m, 3H), 1.80-1.67 (m, 1H), 1.56-1.52 (m, 1H), 0.89 (s, 9H), 0.14-0.09 (m, 6H); $^{13}$C NMR (CDCl$_3$, 75 MHz) δ 143.1, 134.8, 134.0, 129.6, 127.3, 127.2, 70.7, 68.7, 49.1, 34.6, 33.1, 25.8, 25.5, 23.9, 21.4, 18.0, −4.5, −4.9; MS (EI) m/z (%) 382 (4), 324 (8), 200 (10), 199 (25), 198 (100), 197 (86), 155 (67), 140 (21), 105 (15), 91 (58), 77 (13), 75 (81), 73 (30), 57 (16), 44 (35); HRMS (EI) calcd for C$_{22}$H$_{37}$NO$_4$SSi (M$^+$-C$_4$H$_9$): 382.1508. Found 382.1496; Anal. Calcd for C$_{22}$H$_{37}$NO$_4$SSi: C, 60.10; H, 8.48. Found C, 59.92; H, 8.28.

The reactions and numbering referred to in Examples 5-14 are depicted in Scheme 4:

Scheme 4

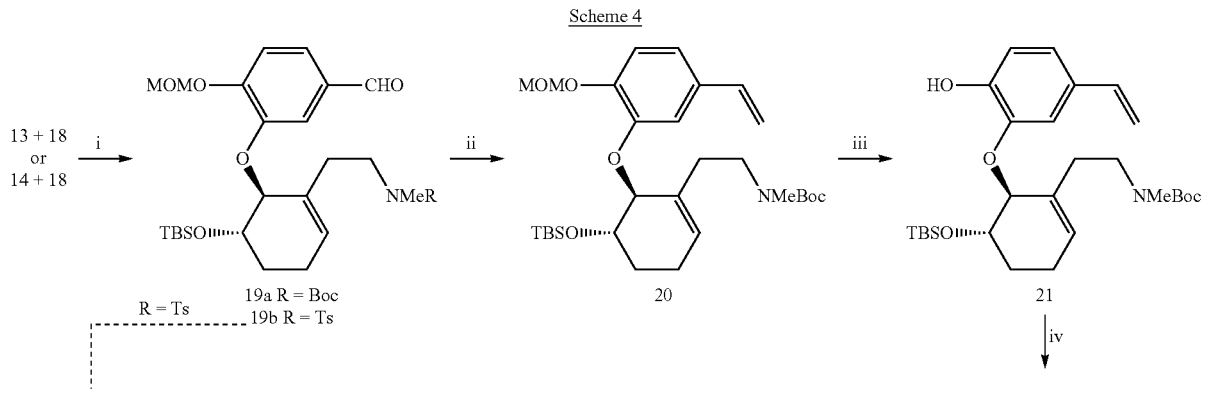

17 18

-continued

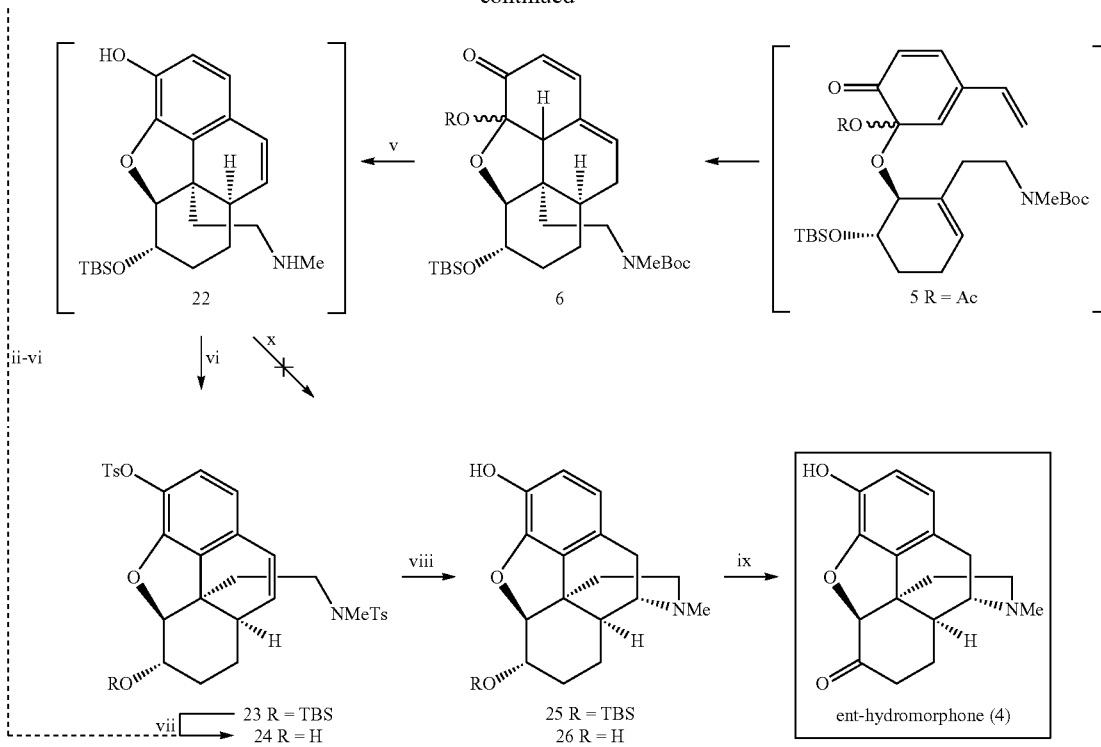

Scheme 4. (i) TMAD, PBu$_3$, 81-85%; (ii) CH$_3$PPh$_3$Br, nBuLi, THF, −78° C. to 0° C. then reflux for 4 h, 82-88%; (iii) ZnBr$_2$, CH$_3$(CH$_2$)$_{10}$CH$_2$SH, CH$_2$Cl$_2$, rt, 10 min., 92%; (iv) Pb(OAc)$_4$, DCE, reflux, 4 h, 50%; (v) TFA, CH$_2$Cl$_2$, 0° C., 15 min; (vi) TsCl, Et$_3$N, CH$_2$Cl$_2$, 0° C. to rt, 45% over two steps; (vii) TBAF, THF, rt, 86%; (viii) Li, tBuOH, NH$_{3(liq)}$, THF, −78° C., 10 min [82-86% for 23 to 25; 93% for 24 to 26]; (ix) tBuOK, PhCOPh, PhCH$_3$/DME, 85° C., 8 h, 44% (x) (a) Hg(OCOCF$_3$)$_2$, CH$_3$CN; rt (b) NaBH$_4$, THF, −78° C.—rt.

Example 5 tert-Butyl(2-((5S,6S)-5-((tert-butyldimethylsilyl) oxy)-6-(5-formyl-2-(methoxymethoxy)phenoxy) cyclohex-1-en-1-yl)ethyl)(methyl) carbamate (19a)

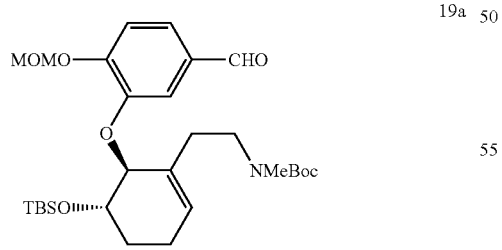

19a

To a solution of alcohol 13 (3.19 g, 8.28 mmol) and phenol 18 (1.66 g, 9.11 mmol) in THF (30 mL) at −10° C. was added PBu$_3$ (2.9 mL, 11.59 mmol) followed by tetramethylazodi-carboxamide (TMAD) (1.9 g, 10.76 mmol). The reaction mixture was slowly warmed to room temperature and was stirred for 18 hours. Solvent was evaporated under reduced pressure and purified by flash column chromatography on silica gel using [hexane/EtOAc (90:10)] as eluent to isolate product 19a (3.7 g, 6.7 mmol, 81%) as a clear oil.

$R_f$=0.39 [hexane/EtOAc (70:30)]; [α]$^{20}_D$=−27.6 (c=1.48, CHCl$_3$); IR (CHCl$_3$, cm$^{-1}$) ν 3681, 3009, 2931, 1726, 1682, 1582, 1506, 1394, 1271, 1159; $^1$H NMR (CDCl$_3$, 300 MHz) δ 9.86 (s, 1H), 7.70 (s, 1H), 7.44 (dd, J=8.1, 1.5 Hz, 1H), 7.28-7.24 (m, 1H), 5.69 (s, 1H), 5.29 (s, 2H), 4.75 (s, 1H), 4.11-4.06 (m, 1H), 3.49 (s, 3H), 3.25-3.17 (m, 2H), 2.72 (s, 3H), 2.35-2.04 (m, 4H), 1.93-1.86 (m, 1H), 1.79-1.70 (m, 1H), 1.41 (s, 9H), 0.81 (s, 9H), 0.00 (s, 3H), −0.09 (s, 3H); $^{13}$C NMR (CDCl$_3$, 75 MHz, rotameric) δ 190.8, 155.7, 152.7, 149.8, 132.4, 131.1, 128.6, 125.8, 125.2, 115.5, 94.8, 80.3, 79.3, 70.4, 60.5, 56.5, 48.5, 34.5, 32.3, 31.7, 28.5, 25.8, 22.8, 18.0, −4.7, −4.8; MS (EI) m/z (%) 312 (37), 268 (50), 237 (29), 136 (34), 57 (51), 44 (100)); HRMS-EI calcd for C$_{29}$H$_{47}$NO$_7$Si: 549.3122 found 549.3115; Anal. Calcd for C$_{29}$H$_{47}$NO$_7$Si: C, 63.36; H, 8.62. Found C, 63.02; H, 8.61.

Example 6

N-(2-((5S,6S)-5-((Tert-butyldimethylsilyl)oxy)-6-(5-formyl-2-(methoxymethoxy)phenoxy) cyclohex-1-en-1-yl)ethyl)-N,4-dimethylbenzenesulfonamide (19b)

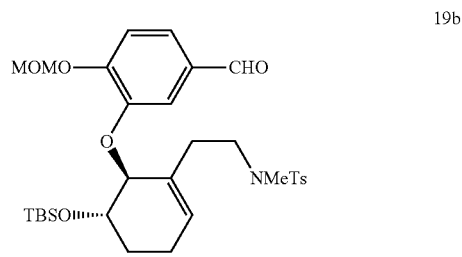

19b

To a solution of alcohol 14 (190 mg, 0.43 mmol) and phenol 18 (102 mg, 0.56 mmol) in THF (6 mL) at −10° C. was added PBu$_3$ (0.15 mL, 0.65 mmol) followed by tetramethylazodicarboxamide (TMAD) (111 mg, 0.65 mmol). The reaction mixture was slowly warmed to room temperature and was stirred for 22 hours. Solvent was evaporated under reduced pressure and purified by flash column chromatography on silica gel using [hexane/EtOAc (80:20)→hexane/EtOAc (50:50)] as eluent to isolate product 19b (130 mg, 0.22 mmol, 50%) as a clear oil.

R$_f$=0.34 [hexane/EtOAc (70:30)]; [α]$^{20}_D$=−21.1 (c=1.5, CHCl$_3$); IR (CHCl$_3$, cm$^{-1}$) v 3028, 3009, 2954, 2930, 2857, 1688, 1596, 1584, 1505, 1463, 1339, 1264, 1160, 1126, 1084; $^1$H NMR (CDCl$_3$, 300 MHz) δ 9.87 (s, 1H), 7.69 (d, J=1.2 Hz, 1H), 7.55-7.45 (m, 3H), 7.28-7.23 (m, 3H), 5.75 (s, 1H), 5.31-5.26 (m, 2H), 4.72 (d, J=4.8 Hz, 1H), 4.14-4.05 (m, 1H), 3.48 (s, 3H), 3.05-3.01 (m, 1H), 2.94-2.88 (m, 1H), 2.62 (s, 3H), 2.50-2.40 (m, 4H), 2.36-2.26 (m, 1H), 2.19-2.13 (m, 2H), 1.89-1.87 (m, 1H), 1.85-1.83 (m, 1H), 0.80 (s, 9H), −0.00 (s, 3H), −0.11 (s, 3H); $^{13}$C NMR (CDCl$_3$, 75 MHz, rotameric) δ 190.9, 152.8, 150.1, 149.4, 143.1, 134.6, 131.8, 130.9, 129.6, 128.9, 127.3, 125.4, 115.4, 115.1, 94.8, 79.9, 70.2, 60.4, 56.5, 49.4, 34.9, 32.4, 28.0, 25.7, 22.7, 21.5, 17.9, −4.9, −5.0; MS (EI) m/z (%) 546 (2), 199 (12), 198 (100), 155 (44), 91 (47), 75 (67), 45 (77); HRMS (EI) calcd for C$_{31}$H$_{45}$NO$_7$SSi (M$^+$-C$_4$H$_9$): 546.1982. Found 546.1976.

Example 7 tert-Butyl (2-((5S,6S)-5-((tert-butyldimethylsilyl)oxy)-6-(2-(methoxy-methoxy)-5-vinylphenoxy)cyclohex-1-en-1-yl)ethyl)(methyl)carbamate (20)

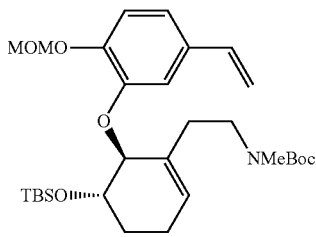

20

To a suspension of Wittig salt CH$_3$P$^+$Ph$_3$Br$^-$ (2.26 g, 6.3 mmol) in THF (20 mL) at −78° C., nBuLi (2.9 mL, 5.8 mmol) was added and the resulting yellow solution was stirred for 15 minutes. It was then warmed to 0° C., and aldehyde 19a (1.58 g, 2.9 mmol) in THF (20 mL) was cannulated into the reaction mixture, which was stirred for another 10 minutes at 0° C. The resulting yellow suspension was heated to reflux for 4 hours whereupon the solvent was evaporated under reduced pressure and column chromatography on silica gel using hexane/EtOAc (80:20) provided 20 (1.3 g, 2.37 mmol, 82%) as a colourless liquid.

R$_f$=0.57 [hexane/EtOAc (70:30)]; [α]$^{20}_D$=−9.4 (c=0.17, CHCl$_3$); IR (CHCl$_3$, cm$^{-1}$) v 3009, 2954, 2930, 2898, 2857, 1683, 1601, 1577, 1506, 1261; $^1$H NMR (CDCl$_3$, 300 MHz, rotameric) δ 7.21-7.20 (m, 1H), 7.07 (d, J=8.1 Hz, 1H), 7.01-6.93 (m, 1H), 6.67-6.57 (m, 1H), 5.67-5.58 (m, 2H), 5.20-5.13 (m, 3H), 4.57 (bs, 1H), 4.08 (bs, 1H), 3.48 (s, 3H), 3.20-3.16 (m, 2H), 2.73 (bs, 3H), 2.36-2.04 (m, 4H), 1.89-1.86 (m, 1H), 1.74-1.67 (m, 1H), 1.42 (s, 9H), 0.83 (s, 9H), −0.01 (s, 3H), −0.08 (s, 3H); $^{13}$C NMR (CDCl$_3$, 75 MHz, rotameric) δ 155.6, 149.2, 147.2, 136.3, 132.6, 132.3, 128.2, 127.8, 119.7, 114.2, 113.7, 116.9, 114.2, 113.7, 112.4, 95.3, 79.9, 79.0, 69.6, 60.3, 56.0, 48.4, 47.7, 34.4, 32.6, 31.8, 28.4, 27.6, 25.7, 22.4, 20.9, 17.9, −4.8, −4.9; MS (EI) m/z (%) 312 (35), 268 (72), 237 (28), 225 (17), 180 (24), 136 (57), 109 (30), 75 (77), 57 (57), 45 (100); HRMS (EI) calcd for C$_{30}$H$_{49}$NO$_6$Si: 547.3329. Found 547.3323; Anal. Calcd for C$_{30}$H$_{49}$NO$_6$Si: C, 65.78; H, 9.02. Found C, 65.52; H, 8.85.

Example 8 tert-Butyl (2-((5S,6S)-5-((tert-butyldimethylsilyl)oxy)-6-(2-hydroxy-5-vinylphenoxy)cyclohex-1-en-1-yl)ethyl)(methyl)carbamate (21)

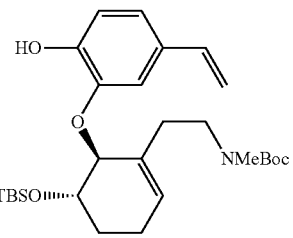

21

To a solution of 20 (1.3 g, 2.4 mmol) in CH$_2$Cl$_2$ (25 mL) at 0° C. was added ZnBr$_2$ (0.59 g, 2.6 mmol) followed by 1-dodecane thiol (1.1 mL, 4.8 mmol). Then the reaction mixture was stirred for 10 minutes, diluted with CH$_2$Cl$_2$ (60 mL), then NaHCO$_3$ (sat) solution was added dropwise and the mixture was filtered through a pad of celite. The aqueous layer was separated and further extracted with CH$_2$Cl$_2$. The combined organic solution was dried with Na$_2$SO$_4$, volatiles were removed in vacuo to provide crude product and column chromatography on silica gel using [hexane/EtOAc (90:10)] provided 21 (1.12 g, 2.22 mmol, 93%) as a clear liquid.

R$_f$=0.27 [hexane/EtOAc (80:20)]; [α]$^{20}_D$=+1.0 (c=3.15, CHCl$_3$); IR (CHCl$_3$, cm$^{-1}$) v 3535, 3297, 2955, 2930, 2858, 1684, 1605, 1508, 1396, 1268, 1161; $^1$H NMR (CDCl$_3$, 300 MHz, rotameric) δ 7.06 (s, 1H), 6.92-6.86 (m, 2H), 6.60 (dd, J=17.4, 10.8 Hz, 1H), 5.65 (s, 1H), 5.56 (d, J=17.7 Hz, 1H), 5.09 (d, J=10.8 Hz, 1H), 4.58 (s, 1H), 4.10-4.06 (m, 1H), 3.71 (bs, 0.6H), 3.15 (bs, 0.8H), 2.95-2.91 (m, 0.6H), 2.75 (s, 3H), 2.33-1.95 (m, 4H), 1.70-1.68 (m, 2H), 1.43 (s, 9H), 0.86 (s, 9H), 0.04 (s, 3H), 0.01 (s, 3H); $^{13}$C NMR (CDCl$_3$, 75 MHz, rotameric) δ 155.7, 146.8, 145.7, 136.7, 130.5, 129.2, 119.7, 115.3, 111.0, 109.8, 79.2, 78.7, 69.6, 68.7, 48.6, 47.6, 44.1, 33.8, 33.1, 31.2, 31.4, 29.6, 29.5, 29.3, 29.0, 28.4, 27.5, 26.7, 25.7, 22.7, 21.9, 17.9, −4.8; MS (EI) m/z (%) 312 (14), 268 (15), 237 (17), 228 (17), 136 (42), 109 (15), 105 (240), 83 (34), 75 (56), 57 (90), 44 (100); HRMS (EI) calcd for C$_{28}$H$_{45}$NO$_5$Si: 503.3067. Found 503.3073; Anal. Calcd for C$_{28}$H$_{45}$NO$_5$Si: C, 66.76; H, 9.00. Found C, 65.85; H, 9.07.

Example 9

(4aS,4a1R,5S,7aR)-4a1-(2-((tert-Butoxycarbonyl)(methyl)amino)ethyl)-5-((tert-butyldimethylsilyl)oxy)-3-oxo-3,3a,3a1,4a,4a1,5,6,7,7a,8-decahydrophenanthro[4,5-bcd]furan-3a-yl acetate (6)

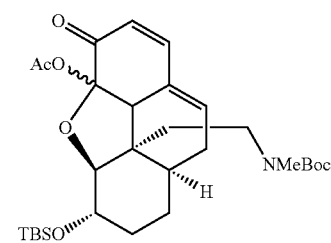

6

A solution of lead tetraacetate (37.9 mg, 0.08 mmol) in DCE (1 mL) was added dropwise to a refluxing solution of 21 (43 mg, 0.08 mmol) in DCE (1 mL). The reaction mixture was stirred for another 4 hours, cooled to room temperature, and then passed through a plug of celite and solvent was evaporated under reduced pressure to obtain the crude product which was purified by column chromatography on silica gel using [hexane/EtOAc (90:10)→hexane/EtOAc (70:30)] as eluent to provide 6 (24 mg, 0.04 mmol, 50%) as a colourless liquid.

$R_f$=0.46 [hexane/EtOAc (70:30)]; $[\alpha]^{20}_D$=−22.0 (c=1.2, CHCl$_3$); IR (CHCl$_3$, cm$^{-1}$) ν 3024, 3009, 2951, 2931, 2858, 1730, 1686, 1625, 1462, 1368, 1252, 1161; $^1$H NMR (300 MHz, CDCl$_3$, rotameric) δ 7.06 (d, J=9.9 Hz, 1H), 6.47 (bt, J=3.6 Hz, 1H), 5.98 (d, J=9.9 Hz, 1H), 4.15-4.05 (m, 1H), 3.42-3.10 (m, 4H), 2.87 (s, 3H), 2.27-2.22 (m, 2H), 2.16 (bs, 1H), 2.13 (s, 3H), 2.04-2.02 (m, 2H), 1.72 (bs, 1H), 1.53-1.51 (m, 1H), 1.47 (s, 9H), 1.14-1.05 (m, 2H), 0.84 (s, 9H), −0.01 (s, 3H), −0.05 (s, 3H); $^{13}$C NMR (75 MHz, CDCl$_3$, rotameric) δ 88.2, 170.9, 155.4, 144.5, 139.0, 134.2, 122.7, 103.9, 90.6, 79.7, 74.2, 73.5, 52.0, 48.6, 45.9, 45.4, 40.7, 39.8, 38.6, 37.3, 34.4, 30.8, 29.4, 28.5, 25.8, 21.3, 20.6, 18.1, −4.6, −5.1; MS (EI) m/z (%) 388 (10), 345 (10), 313 (12), 287 (25), 171 (15), 83 (12), 75 (23), 73 (45), 59 (34), 57 (87), 44 (100); HRMS (EI) calcd for C$_{30}$H$_{47}$NO$_7$Si (M$^+$-C$_2$H$_4$O$_2$): 501.2911. Found 501.2910; Anal. Calcd for C$_{30}$H$_{47}$NO$_7$Si: C, 64.14; H, 8.43. Found C, 64.03; H, 8.45.

Example 10

(4aS,4a1R,5S,7aR)-5-((tert-Butyldimethylsilyl)oxy)-4a1-(2-(N,4-dimethylphenylsulfonamido)ethyl)-4a,4a1,5,6,7,7a-hexahydro phenanthro [4,5-bcd]furan-3-yl 4-methylbenzenesulfonate (23)

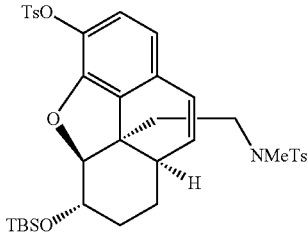

A solution of 6 (16 mg, 0.028 mmol) in CH$_2$Cl$_2$ (1.5 mL) was cooled in an ice bath and TFA (0.5 mL) was added dropwise. The reaction mixture was stirred for 10 minutes, diluted with CH$_2$Cl$_2$ (4.5 mL) and the pH of the reaction mixture was adjusted to ~7 using saturated Na$_2$CO$_3$ solution. The organic layer was separated, washed with water, dried over Na$_2$SO$_4$ and evaporated in vacuo to obtain the crude product (22) which was immediately taken to next step without further purification.

To a solution of 22 in CH$_2$Cl$_2$ cooled in an ice bath, was added Et$_3$N (6.3 μL, 0.045 mmol) and TsCl (8.6 mg, 0.045 mmol) and the resulting reaction mixture was stirred for 10 hours. The solvent was evaporated under reduced pressure and the crude product was purified by column chromatography on silica gel using [hexane/EtOAc (90:10)→hexane/EtOAc (80:20)] as eluent to provide 23 (9 mg, 0.013 mmol, 46% over two steps) as a light yellow oil.

$R_f$=0.47 [hexane/EtOAc (70:30)]; $[\alpha]^{20}_D$=−106.5 (c=0.42, CHCl$_3$); IR (CHCl$_3$, cm$^{-1}$) ν 3027, 2929, 2857, 1599, 1490, 1446, 1378, 1341, 1274, 1221, 1158; $^1$H NMR (300 MHz, CDCl$_3$) δ 7.78 (d, J=8.4 Hz, 2H), 7.61 (d, J=8.1 Hz, 2H), 7.31-7.26 (m, 4H), 6.84 (d, J=8.1 Hz, 1H), 6.59 (d, J=8.1 Hz, 1H), 6.35 (d, J=9.6 Hz, 1H), 5.92 (dd, J=9.6, 5.7 Hz, 1H), 4.36 (d, J=6.9 Hz, 1H), 3.31-3.23 (m, 1H), 3.05-2.95 (m, 1H), 2.82-2.72 (m, 1H), 2.59 (s, 3H), 2.44 (s, 3H), 2.40 (s, 3H), 2.36-2.34 (m, 1H), 1.77-1.68 (m, 2H), 1.63-1.55 (m, 3H), 1.25-1.17 (m, 1H), 0.88 (s, 9H), 0.08 (s, 3H), −0.01 (s, 3H); $^{13}$C NMR (150 MHz, CDCl$_3$) δ 148.2, 145.3, 143.3, 134.6, 133.0, 132.8, 132.7, 129.7, 129.6, 129.2, 128.9, 128.8, 127.4, 124.1, 122.5, 117.7, 98.2, 73.9, 46.1, 44.7, 39.7, 35.8, 34.8, 29.8, 29.7, 26.6, 25.8, 21.7, 21.5, 18.1, −4.6, −5.0; MS (EI) m/z (%) 653 (3), 198 (34), 155 (12), 149 (19), 124 (28), 123 (13), 100 (42), 92 (17), 91 (58), 83 (16), 57 (35), 43 (100); HRMS (EI) calcd for C$_{37}$H$_{47}$NO$_7$S$_2$Si (M$^+$-C$_4$H$_9$): 652.1859. Found 652.1852; Anal. Calcd for C$_{37}$H$_{47}$NO$_7$S$_2$Si: C, 62.59; H, 6.67. Found C, 62.52; H, 6.63.

Example 11

(4aS,4a1R,5S,7aR)-4a1-(2-(N,4-Dimethylphenylsulfonamido)ethyl)-5-hydroxy-4a,4a1,5,6,7,7a-hexahydrophenanthro[4,5-bcd]furan-3-yl 4-methylbenzenesulfonate (24)

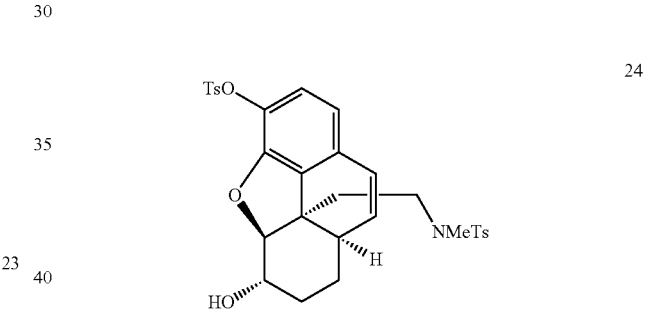

To a mixture of 23 (141 mg, 0.19 mmol) and THF (5 mL) at room temperature was added tetrabutylammonium fluoride (TBAF) solution in THF (0.34 mL, 0.34 mmol). The resulting mixture was stirred for 6 hours and the solvent was evaporated under reduced pressure to provide the crude product, which was purified by column chromatography on silica gel using [hexane/EtOAc (70:30)→hexane/EtOAc (50:50)] as eluent to provide 24 (101 mg, 0.17 mmol, 86%) as a clear oil.

$R_f$=0.29 [hexane/EtOAc (50:50)]; $[\alpha]^{18}_D$=−20.4 (c=0.55, CHCl$_3$); IR (CHCl$_3$, cm$^{-1}$) ν 3518, 3033, 2926, 2861, 1597, 1489, 1445, 1335, 1191, 1177, 1088; $^1$H NMR (300 MHz, CDCl$_3$) 67.76 (d, J=8.4 Hz, 2H), 7.58 (d, J=8.1 Hz, 2H), 7.33-7.26 (m, 4H), 6.78 (d, J=8.1 Hz, 1H), 6.58 (d, J=8.4 Hz, 1H), 6.35 (d, J=9.6 Hz, 1H), 5.93 (dd, J=9.6, 5.7 Hz, 1H), 4.48 (d, J=7.2 Hz, 1H), 3.08-2.98 (m, 2H), 2.84-2.74 (m, 1H), 2.57 (s, 3H), 2.47-2.36 (m, 8H), 1.88-1.56 (m, 4H), 1.27-1.15 (m, 1H), 0.89-0.76 (m, 1H); $^{13}$C NMR (75 MHz, CDCl$_3$) δ 47.9, 145.6, 143.4, 134.3, 133.0, 132.6, 129.7, 129.3, 129.1, 128.7, 127.4, 123.8, 122.5, 117.9, 98.0, 76.7, 72.9, 46.1, 44.7, 39.3, 35.2, 34.8, 27.8, 26.9, 21.7, 21.5; MS (EI) m/z (%) 595 (1), 440 (4), 384 (3), 229 (7), 198 (10), 155 (35), 139 (13), 124 (20), 97 (13), 92 (18), 91 (100), 69 (21), 57 (30); HRMS (EI) calcd for C$_{31}$H$_{33}$NO$_7$S$_2$: 595. 1698. Found 595. 1693.

Example 12

(4S,4aS,7S,7aS,12bR)-7-((tert-Butyldimethylsilyl)oxy)-3-methyl-2,3,4,4a,5,6,7,7a-octahydro-1H-4,12-methanobenzofuro[3,2-e]isoquinolin-9-ol (25)

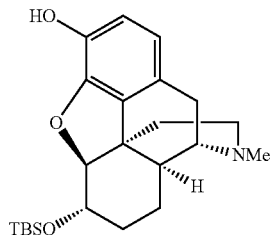

To a mixture of tBuOH (64 µL, 0.62 mmol) and THF (2 mL) at −78° C. was added liquid $NH_3$ (~15 mL) and Li wire (37 mg, 5.3 mmol). The resulting blue color reaction mixture was stirred for five minutes and 23 (35 mg, 0.05 mmol) in THF (2 mL) was added dropwise. The reaction mixture was stirred for another 10 minutes while it remained blue in color. Then 2 g of $NH_4Cl$ was added as a solid, followed by 10 mL of MeOH and 20 mL of saturated $NH_4Cl$ solution. This mixture was then washed three times with $CH_2Cl_2$ (20 mL), the combined organic layers were washed with saturated NaCl solution, and dried over $Na_2SO_4$. The solvent was evaporated under reduced pressure to provide the crude product, which was purified by column chromatography on silica gel using [$CH_2Cl_2$/MeOH (95:5)→$CH_2Cl_2$/MeOH (90:10)] as eluent to provide 25 (16 mg, 0.04 mmol, 82%) as a colourless oil.

$R_f$=0.24 [$CH_2Cl_2$/MeOH (90:10)]; $[\alpha]^{20}_D$=+70.5 (c=0.8, $CHCl_3$); IR ($CHCl_3$, $cm^{-1}$) ν 3688, 3586, 2953, 2931, 2858, 1624, 1604, 1505, 1455, 1220, 1119, 1098; $^1$H NMR (600 MHz, $CDCl_3$) δ 6.70 (d, J=8.4 Hz, 1H), 6.58 (d, J=7.8 Hz, 1H), 4.91 (bs, 1H), 4.31 (d, J=6.6 Hz, 1H), 3.39-3.35 (m, 1H), 3.25 (d, J=2.4 Hz, 1H), 2.98 (d, J=18.6 Hz, 1H), 2.68 (dd, J=12, 4.2 Hz, 1H), 2.46 (s, 3H), 2.44-2.43 (m, 1H), 2.28-2.22 (m, 2H), 2.03 (s, 1H), 1.95-1.90 (m, 1H), 1.67-1.65 (m, 2H), 1.53-1.50 (m, 1H), 1.39-1.32 (m, 1H), 0.88 (s, 9H), 0.10 (s, 3H), 0.01 (s, 3H); $^{13}$C NMR (150 MHz, $CDCl_3$) δ 143.0, 139.9, 129.9, 124.5, 119.2, 117.0, 97.3, 73.7, 59.5, 46.9, 42.9, 42.2, 41.7, 34.7, 31.6, 25.8, 23.4, 20.4, 18.1, −4.5, −4.8; MS (EI) m/z (%) 401 (3), 120 (29), 118 (32), 87 (92), 85 (80), 83 (76), 60 (30), 47 (100), 43 (44); HRMS (EI) calcd for $C_{23}H_{35}NO_3Si$: 401.2386. Found 401.2375.

Example 13

(4S,4aS,7S,7aS,12bR)-3-methyl-2,3,4,4a,5,6,7,7a-octahydro-1H-4,12-methanobenzofuro[3,2-e]isoquinoline-7,9-diol (26)

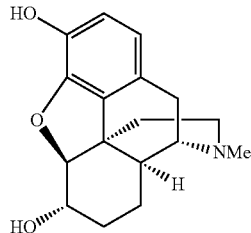

To a mixture of tBuOH (35 µL, 0.34 mmol) and THF (2 mL) at −78° C. was added liquid $NH_3$ (~15 mL) and Li wire (20 mg, 2.85 mmol). The resulting blue colour reaction mixture was stirred for five minutes and 24 (20 mg, 0.03 mmol) in THF (2 mL) was added dropwise. The reaction mixture was stirred for another 10 minutes while the reaction mixture remained blue in color. Then 2 g $NH_4Cl$ was added as a solid, followed by 10 mL of MeOH and 20 mL of saturated $NH_4Cl$ solution. This mixture was then washed three times with $CH_2Cl_2$ (20 mL), the combined organic washes were washed with saturated NaCl solution and was further dried over $Na_2SO_4$. The solvent was evaporated under reduced pressure to provide the crude product, which was purified by column chromatography on silica gel using [$CH_2Cl_2$/MeOH (90:10) →$CH_2Cl_2$/MeOH (80:20)→MeOH] as eluent to provide 26 (9.1 mg, 0.03 mmol, 93%) as a white solid.

m.p.>200° C.; $R_f$=0.15 [$CH_2Cl_2$/MeOH (80:20)]; $[\alpha]^{20}_D$=+57.0 (c=0.35, MeOH); IR ($CHCl_3$, $cm^{-1}$) ν 3311, 2923, 1599, 1462, 1313, 1255, 1084; $^1$H NMR (600 MHz, MeOD) δ 6.71 (d, J=7.8 Hz, 1H), 6.66 (d, J=7.8 Hz, 1H), 4.33 (d, J=6.6 Hz, 1H), 3.66 (s, 1H), 3.16 (d, J=19.2 Hz, 1H), 3.02 (d, J=11.4 Hz, 1H), 2.78 (s, 3H), 2.64-2.60 (m, 1H), 2.39 (d, J=9.6 Hz, 1H), 2.10-2.05 (m, 1H), 1.81 (d, J=10.6 Hz, 2H), 1.68-1.66 (m, 1H), 1.43-1.31 (m, 2H), 1.03-0.97 (m, 1H), 0.93-0.90 (m, 1H); $^{13}$C NMR (150 MHz, MeOD) δ 142.9, 140.9, 128.5, 122.1, 119.3, 117.5, 95.5, 72.1, 60.9, 47.2, 42.1, 40.6, 40.4, 33.2, 30.1, 22.9, 20.8; MS (EI) m/z (%) 287 (92), 286 (23), 230 (22), 228 (10), 164 (17), 149 (15), 97 (17), 84 (26), 70 (32), 57 (53), 43 (100); HRMS (EI) calcd for $C_{17}H_{21}NO_3$: 287.1521. Found 287.1519.

Example 14

(4S,4aS,7aS,12bR)-9-Hydroxy-3-methyl-2,3,4,4a,5,6-hexahydro-1H-4,12-methanobenzofuro[3,2-e]isoquinolin-7(7aH)-one (4)

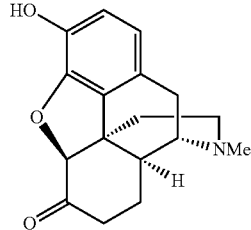

To a suspension of 26 (8 mg, 0.028 mmol) and benzophenone (10.2 mg, 0.056 mmol) in a mixture of toluene (1 mL) and DME (1 mL) was added potassium tert-butoxide (18 mg, 0.16 mmol) at room temperature. The resulting reaction mixture was heated at 85° C. for 8 hours and then the solvent was evaporated under reduced pressure to obtain the crude reaction mixture, which was purified by column chromatography on silica gel using [$CH_2Cl_2$/MeOH (95:5)→$CH_2Cl_2$/MeOH (90:10)] as eluent to provide 4 (3.5 mg, 0.012 mmol, 44%) as a white solid along with unreacted starting material 26 (4 mg, 0.014 mmol, 53%). The physical and spectral properties of 4 were matched with those given in the literature.[7]

m.p.>200° C.; [lit.[3] m.p. 266-267° C. (ethanol)]; $R_f$=0.41 [$CH_2Cl_2$/MeOH (80:20)]; $[\alpha]^{20}_D$+190.0 (c=0.13, dioxane), [lit.[3] $[\alpha]^{25}_D$=−194 (c=0.98, dioxane); $^1$H NMR (300 MHz, MeOD) δ6.70 (dd, J=14.1, 8.4 Hz, 2H), 4.61 (s, 1H), 3.56 (bs, 1H), 3.14 (d, J=19.2 Hz, 1H), 2.95-2.89 (m, 1H), 2.77-2.72 (m, 4H), 2.60-2.52 (m, 1H), 2.36-2.32 (m, 1H), 2.00-1.87 (m, 1H), 1.80 (dd, J=13.2, 2.7 Hz, 1H), 1.68 (dd, J=13.2, 2.4 Hz, 1H), 1.45-1.40 (m, 1H), 1.14-1.05 (m, 1H), 0.92-0.89 (m, 1H).

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS
REFERRED TO IN THE SPECIFICATION

[1] For reviews of morphine alkaloid syntheses and discussion of strategies see: (a) U. Rinner, T. Hudlicky, *Top. Curr. Chem.* 2012, 309, 33-66; (b) J. Zezula, T. Hudlicky, *Synlett* 2005, 388-405; (c) D. F. Taber, T. D. Neubert, M. F. Schlecht, in *Strategies and Tactics in Organic Synthesis*, Vol. 5 (Ed.: H. Michael), Elsevier, London, 2004, pp. 353-389; (d) T. Hudlicky, *J. Heterocyclic Chem.* 2000, 37, 535-539; (e) B. H. Novak, T. Hudlicky, J. W. Reed, J. Mulzer, D. Trauner, *Curr. Org. Chem.* 2000, 4, 343-362; (f) T. Hudlicky, G. Butora, S. P. Fearnley, A. G. Gum, M. R. Stabile, in *Studies in Natural Products Chemistry*, Vol. 18, Part K (Ed.: R. Atta-ur), Elsevier, Amsterdam, 1995, pp. 43-154; (g) M. Maier, in *Organic Synthesis Highlights II*, (Ed.: H. Waldmann), VCH, Weinheim, 1995, pp. 357-369.

[2] A. M. Sawayama, H. Tanaka, T. J. Wandless, J. Org. Chem. 2004, 69, 8810-8820.

[3] J. G. Buchanan, D. G. Hill, R. H. Wightman, I. K. Boddy, B. D. Hewitt, *Tetrahedron* 1995, 51, 6033-6050.

[4] H. Leisch, A. T. Omori, K. J. Finn, J. Gilmet, T. Bissett, D. Ilceski, T. Hudlicky, *Tetrahedron* 2009, 65, 9862-9875.

[5] J. Duchek, T. G. Piercy, J. Gilmet, T. Hudlicky, *Can. J. Chem.* 2011, 89, 709-729.

[6] G. J. Zylstra, D. T. Gibson, *J. Biol. Chem.* 1989, 264, 14940-14946.

[7] H. Rapoport, R. Naumann, E. R. Bissell, R. M. Bonner, *J. Org. Chem.* 1950, 15, 1103-1107.

The invention claimed is:

1. A process for the preparation of a compound of Formula I comprising treating a compound of Formula II under [4+2] intramolecular cycloaddition conditions:

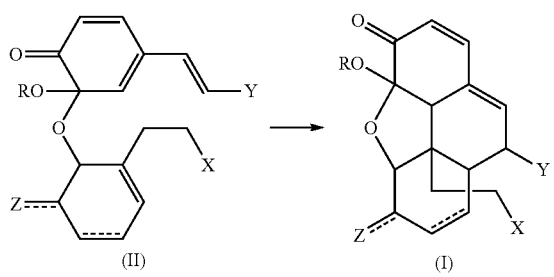

wherein:
- - - - represents a single or double bond;
Z is O when Z - - - - represents a double bond and Z is OPG$^1$ when Z - - - - represents a single bond;
OR represents a leaving group;
at least one of Y and X is NMePG$^2$ and the other is LG, or Y is H and X is NMePG$^2$;
PG$^1$ and PG$^2$ are, independently, protecting groups; and
LG is a leaving group, and
one or more available hydrogens in the compounds of Formulae I and II is/are optionally replaced with F and/or one or more of available atoms in the compounds of Formulae I and II is/are optionally replaced with an isotopic label.

2. The process of claim 1, wherein the compound of Formula II is prepared by converting a compound of Formula III into a compound of Formula II by oxidative dearomatization:

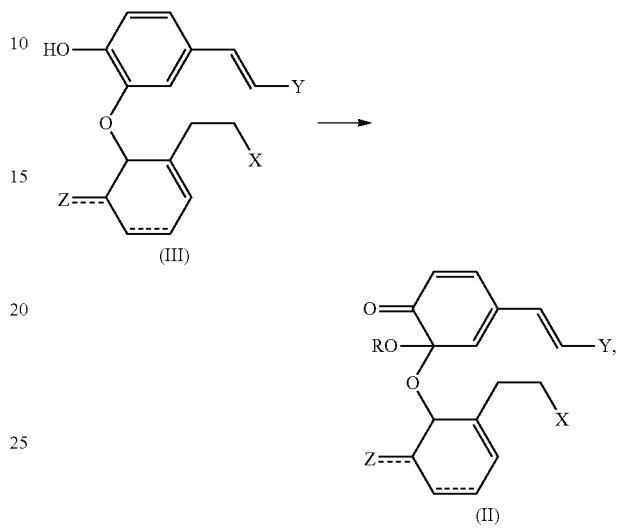

wherein - - - -, X, Y, Z and OR are as defined in claim 1.

3. The process of claim 2, wherein the compound of the Formula III is prepared by reacting a compound of the Formula IV with a compound of the Formula V under Mitsunobu reaction conditions to provide a compound of the Formula VI followed by Wittig homologation of the CHO group and removal of PG$^3$:

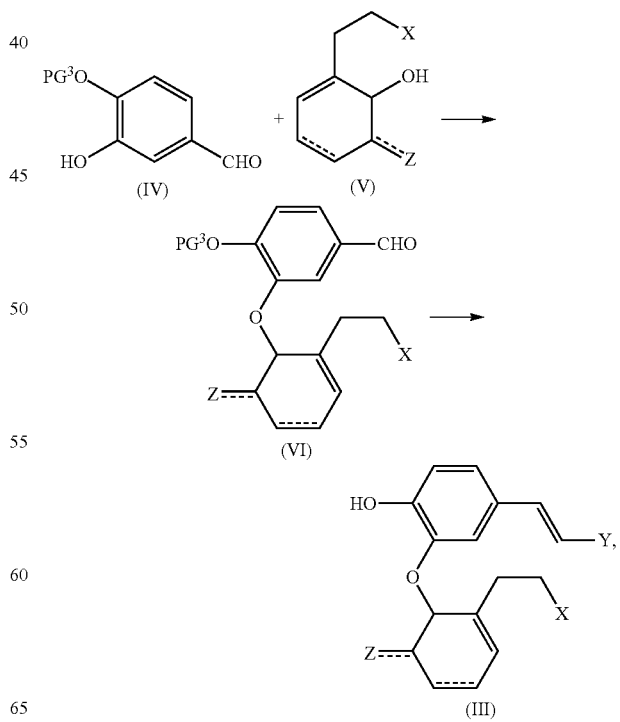

wherein 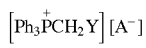, X, Y and Z are as defined in claim 1; and PG³ is a protecting group.

4. The process of claim 3, wherein the Wittig homologation of the CHO group is performed by reacting a compound of the Formula VI with a Wittig reagent of the Formula VII:

$$[Ph_3\overset{+}{P}CH_2Y][A^-] \qquad (VII)$$

wherein Y is as defined in claim 1; and

[A⁻] is a suitable counteranion under Wittig reaction conditions.

5. The process of claim 2, wherein the compound of the Formula III wherein Y is H is prepared by Wittig homologation of the CHO group in a compound of Formula X to provide a compound of Formula XI, followed by selective removal of PG⁵ to provide a compound of Formula XII, then reacting the compound of Formula XII with a compound of Formula V under Mitsunobu reaction conditions and removal of PG⁴:

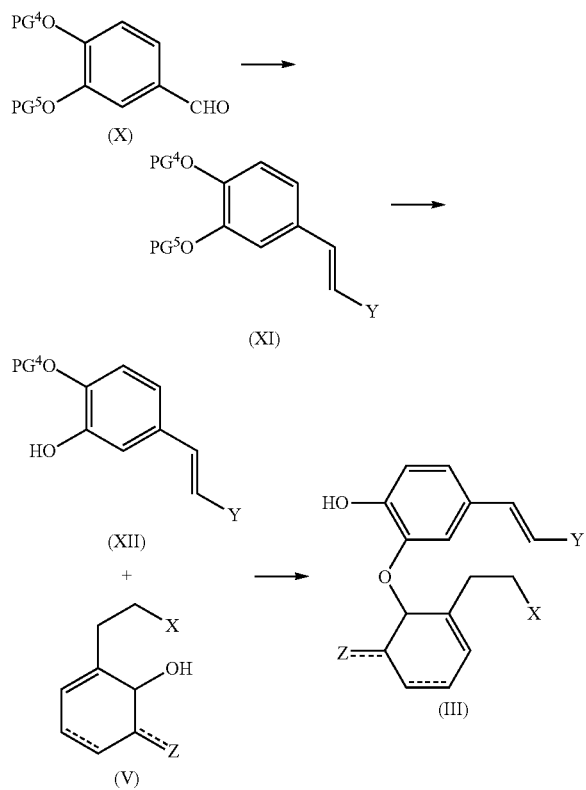

wherein:

----, X, Y and Z are as defined in claim 1; and

PG⁴ and PG⁵ are protecting groups that are removable under different conditions.

6. The process of claim 5, wherein the Wittig homologation of the CHO group is performed by reacting a compound of the Formula X with a Wittig reagent of the Formula VII:

$$[Ph_3\overset{+}{P}CH_2Y][A^-] \qquad (VII)$$

wherein Y is as defined in claim 1; and

[A⁻] is a suitable counteranion under Wittig reaction conditions.

7. The process of claim 1, wherein Z ---- and C ---- C both represent single bonds and Z is OPG¹.

8. The process of claim 1, wherein Y is H and X is NMePG².

9. The process of claim 3, wherein X is NMePG² or LG, Z is O, Z ---- is a double bond and C ---- C is a single bond and the compound of Formula V is prepared by treating a compound of the Formula VIII under Birch reduction conditions to provide a compound of the Formula IX and treating the compound of the Formula IX under Davis hydroxylation conditions to provide the compound of the Formula V, wherein X is NMePG² or LG, Z is O, Z ---- is a double bond and C ---- C is a single bond:

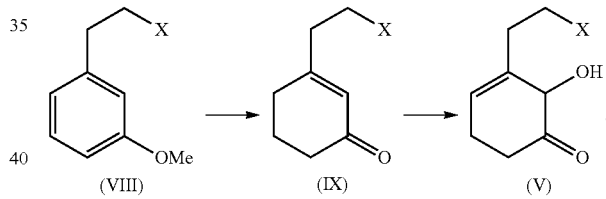

10. The process of claim 1, wherein X is LG and Y is NMePG².

11. The process of claim 1, wherein the stereochemistry of the compound of Formula II is selected so that the compound of Formula I has the same stereochemistry as that found in hydromorphone.

12. The process of claim 1, wherein the stereochemistry of the compound of Formula II is selected so that the compound of Formula I has the same stereochemistry as that found in ent-hydromorphone.

* * * * *